United States Patent
Schön et al.

[11] Patent Number: 6,162,881
[45] Date of Patent: Dec. 19, 2000

[54] INITIATORS FOR CATIONIC POLYMERIZATION

[75] Inventors: Lothar Schön, Neunkirchen; Wolfgang Rogler, Möhrendorf; Volker Muhrer, Fürth; Manfred Fedtke, Merseburg; Andreas Palinsky, Garbsen, all of Germany

[73] Assignee: Siemens Aktiegesellschaft, Munich, Germany

[21] Appl. No.: 09/105,144

[22] Filed: Jun. 26, 1998

[30] Foreign Application Priority Data

Jun. 30, 1997 [DE] Germany .................. 197 27 820

[51] Int. Cl.[7] ................... C08J 4/06; C08F 4/40; C08F 2/46; C08T 3/28; G08C 1/73

[52] U.S. Cl. ................ 526/94; 526/100; 526/205; 526/222; 522/14; 522/16; 522/31; 430/281.1

[58] Field of Search ................. 522/31, 14, 16; 430/281.1; 526/100, 205, 222, 94

[56] References Cited

U.S. PATENT DOCUMENTS

| | | | |
|---|---|---|---|
| 4,147,552 | 4/1979 | Specht et al. | 96/115 R |
| 5,073,476 | 12/1991 | Meier et al. | 430/280 |
| 5,141,969 | 8/1992 | Saeva et al. | 522/31 |
| 5,484,810 | 1/1996 | Grisar et al. | 514/456 |
| 5,738,974 | 4/1998 | Nagasaka et al. | 430/278.1 |
| 5,811,218 | 9/1998 | Kaji et al. | 430/281.1 |

FOREIGN PATENT DOCUMENTS

| | | |
|---|---|---|
| 0 370 693 A2 | 5/1990 | European Pat. Off. . |
| 0 704 764 | 2/1995 | European Pat. Off. . |
| 0636939 | 2/1995 | European Pat. Off. . |

*Primary Examiner*—David W. Wu
*Assistant Examiner*—Tanya Zalukaeva
*Attorney, Agent, or Firm*—Kenyon & Kenyon

[57] ABSTRACT

New initiators which are suitable for cationic polymerization have the following structure:

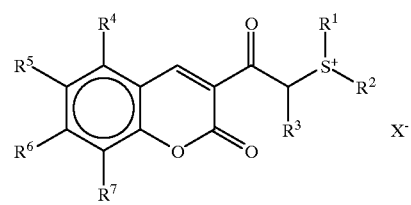

such that following apply:
  $R^1$ and $R^2$ are alkyl or cycloalkyl or they, together with the S atom, form a heterocyclic ring,
  $R^3$ is H or alkyl,
  $R^4$, $R^5$, $R^6$, and $R^7$ are H, alkyl, or alkoxy,
  $X^-$ is a non-nucleophilic anion.
Reaction resin mixtures with initiators of this type contain, in addition to a cationically polymerizable monomer and/or oligomer, 0.01 to 10% by mass of the initiator.

10 Claims, No Drawings

INITIATORS FOR CATIONIC POLYMERIZATION

FIELD OF THE INVENTION

The invention relates to new initiators for cationic polymerization, as well as to cationically hardenable reaction resin mixtures containing these initiators and their use.

BACKGROUND OF THE INVENTION

Reaction resin mixtures hardenable using ultraviolet (UV) light in accordance with a cationic mechanism are becoming increasingly important technically, because they yield molded materials having excellent thermal-mechanical properties. The chemical basis for these reaction resin mixtures are compounds which contain oxirane rings, such as epoxy resins and/or vinyl ethers. Whereas reaction resin mixtures on the basis of vinyl ethers are distinguished by their rapid speed of reaction (in hardening), reaction resin mixtures on the basis of epoxides prove to be advantageous due to a more favorable performance with respect to shrinkage in the hardening process.

In the hardening process of reaction resin mixtures, the UV light is absorbed by a photoinitiator, which, as a result of subsequent reactions, forms carbocations or protons; these are the actual active species for the start of the polymerization. Conventional photoinitiators for cationic polymerization are, for example, triarylsulfonium salts. Although they possess good reactivity in response to UV irradiation, they are thermally (i.e., in response to an increase in the temperature) very stable and therefore incapable of thermally initiating the cationic polymerization.

Thermal hardening is always necessary when it is impossible to irradiate all areas of the resin. For example, this is the case when thicker layers are to be produced or when light-diffusing or light-absorbing additives, such as fillers, pigments and dyes are contained in the reaction resin mixture. In those cases, the light is highly absorbed or diffused in the layer regions closer to the surface, so that the light transmitted into the deeper layer regions is not sufficient to bring about a (complete) hardening.

In addition, a UV hardening is impossible when, in accordance with the method, areas are present which are not accessible to direct irradiation. In gluing together non-transparent joining parts as well as electronic components and assemblies, the adhesive agent is applied first, and then the component part is mounted. By irradiation using UV light, in this context, only those edge areas can be hardened where the adhesive agent oozes out; underneath the component part, the hardening must be brought about through an additional process, e.g., thermally induced. The situation is comparable when components and assemblies, for protection against environmental influences, are provided with a protective lacquer. For due to capillary action, the lacquer migrates under the component parts, and there, once again, it cannot be hardened by irradiation.

Reaction resin mixtures that are hardenable by UV light can be used for the production of complex plastic models by stereo lithography with the aid of 3D CAD data. In this context, the surface of a liquid photopolymer, hardenable by laser light, is irradiated patternwise by a computer-controlled laser beam, a first layer of the three-dimensional structure to be produced being cured. Subsequently, this layer is coated with fresh photopolymer and is once again irradiated patternwise by the laser. In this way, a second hardened layer of the three-dimensional structure arises, joining with the first one. This process continues until the entire structure is produced, which, in this context, expands into the photopolymer bath. The "green part" formed in this way and only partly cured, is subsequently cured to a great extent as a result of longer irradiation by UV-A light.

In this method, photopolymers based on epoxy resins are advantageously used, the photopolymers demonstrating a more favorable performance with respect to shrinkage in comparison to polymers based on acrylate, so that greater dimensional and form stability can be achieved. In addition, a second cure of the partly hardened green parts is also possible by raising the temperature. This thermal hardening is successful only when all the areas to be strengthened were previously irradiated. Purely thermal hardening, on the other hand, is impossible in conventional photopolymers using triarylsulfonium salts.

However, the possibility of a thermal hardening is a goal because, in the case of a partial irradiation, for example for producing contours and grids, considerable time can be saved in comparison to an all-over irradiation. The assumption, in this context, however, is that the non-irradiated areas can be cured by a subsequent thermal process, because otherwise molded-material properties are only achieved to an inadequate degree. A second irradiation of these areas in the interior of thicker parts is impossible because the light will be absorbed by the photoinitiator in the edge layers and thus is not available for a photochemical process in the interior of the parts.

The speed of hardening in the cationic polymerization of epoxy resins is slower than in polymerization of acrylates, and also a higher UV dose is required for the hardening. Therefore, the most powerful UV lasers possible must be used. These are available, for example, using argon-ion lasers (having wavelengths of 351 and 364 nm) as well as using frequency-tripled Nd:YAG lasers (having a wavelength of 351 nm), but in these wavelengths, the absorption capacity of the triarylsulfonium salts, which are usually employed, is too slight to be able to effectively form cations or protons.

From European Patent Application No. 0 370 693 A2, it is known to use as photoinitiators onium salts, which form a Brønsted acid under irradiation with visible light. These are sulfonium, arsonium, ammonium, and phosphonium salts (having an S, As, N or P atom), which contain a chromophore which absorbs visible light, the chromophore being separated from the S, As, N or P atom by an isolating group, which prevents a π-resonance (between the chromophore and the other substituents). The onium salts additionally contain at least one substituent which represents an electron-attracting grouping and has an unoccupied molecular orbital at a lower energy level than the light-absorbing chromophore. Examples of the onium salts of this type are: 4-cyanobenzyl-2-[5-naphthacenyl] benzylphenyl-sulfonium hexafluorophosphate and -trifluoromethane sulfonate as well as phenyl-p-cyanobenzyl-4-[6,7-dimethoxycumarin-methyl]sulfonium hexafluorophosphate and -trifluoromethane sulfonate. Activation of the onium salts by UV light does not take place, nor does a purely thermal formation, i.e., without previous irradiation, of the Brønsted acids.

SUMMARY OF THE INVENTION

The object of the invention is to indicate initiators for cationic polymerization, i.e., for the hardening of cationically polymerizable reaction resin mixtures, initiators which are activatable both by UV irradiation, in particular in the area of approximately 300 to 400 nm, as well as thermally;

in addition, the reaction resin mixtures containing the initiators should be stable in storage.

This is achieved according to the present invention in that the initiators are compounds having the following structure:

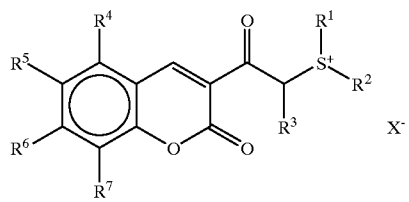

such that the following apply:
- $R^1$ and $R^2$ are (independently from each other) alkyl having 1 to 9 C atoms (linear or branched) or cycloalkyl having 4 to 9 C atoms, or together they form a divalent aliphatic group having 4 to 7 C atoms, i.e., together with the S atom, a heterocyclic ring,
- $R^3$ is H or alkyl having 1 to 9 C atoms (linear or branched), $R^4$, $R^5$, $R^6$, and $R^7$ are (independently from each other) H, alkyl, or alkoxy, in each case, having 1 to 9 C atoms (linear or branched),
- $X^-$ is a non-nucleophilic anion, such as hexafluoroantimonate ($SbF_6^-$), -arsenate ($AsF_6^-$) and -phosphate ($PF_6^-$), tetraphenyl-borate ($B(C_6H_5)_4^-$), tetra(perfluorophenyl)-borate ($B(C_6F_5)_4^-$) or trifluoromethane sulfonate ($CF_3-SO_3^-$)

DETAILED DESCRIPTION OF THE INVENTION

The initiators according to the invention are derivatives of cumarin (2H-1-benzopyran-2-one) having a sulfonium group in the 3 position. These initiators, when dissolved in cationically polymerizable monomers or oligomers, absorb UV light, the maximum absorption being in the range of approximately 300 to 400 nm. As a consequence of the UV irradiation, reactive cations or protons are formed. These reactive species are also released in response to a rise in temperature, i.e., when the initiators, dissolved in cationically polymerizable monomers or oligomers, are exposed to a temperature treatment.

The new initiators can advantageously be produced, in a first step, by reacting ω-halogen-3-acetyl cumarin, which optionally has the desired substituents ($R^3$ to $R^7$), with a dialkyl sulfide (having $R^1$ and $R^2$), which can be a cyclic compound (e.g.: $R^1+R^2=(CH_2)_4$); in this manner, the corresponding dialkyl sulfonium halogenide is formed. This reaction can be conducted both in a suitable solvent as well as in bulk. It is advantageous to use a solvent in which both starting compounds are homogeneously soluble, and from which the sulfonium salt precipitates. For the reaction, both ω-chlorine as well as ω-bromine-3-acetyl cumarins can be used; the ω-bromine derivatives are preferred. The resulting dialkyl sulfonium halogenide is usually isolated and purified by recrystallization. In a second step, the halogenide ion is exchanged for a non-nucleophilic anion. For this purpose, the dialkyl sulfonium halogenide is dissolved, for example, in methanol and is added to a solution of an equimolar quantity of sodium hexafluoroantimonate in methanol. The sulfonium hexafluoroantimonate, in this context, precipitates and can be filtered off and recrystallized.

The ω-halogen-3-acetyl cumarins used for the synthesis of the initiators can be produced, in a condensation reaction, from the corresponding salicylaldehyde and acetoacetic ester. This reaction can be performed in an alcohol solution using pyridine as a catalyst at approximately 60° C. Subsequently, the halogenization of the acetyl residue takes place, in a generally known manner, for example, using bromine in an ether solution.

The initiators according to the present invention can be employed, in principle, when a reaction is brought about by cations or protons. This is particularly the case with cationic polymerization of monomers and oligomers that have been made capable thereof. Compounds of this type are known, for example, from European Patent Specification No. 0 126 712 B1.

Cationically hardenable reaction resin mixtures according to the present invention contain a cationically polymerizable monomer and/or oligomer (Component A) and—with reference to Component A—0.01 to 10% by mass of the initiator; the monomers and oligomers can be present in mixture. To modify the processing and molded-material properties, the mixtures can contain additives such as mineral and organic fillers, dyes, pigments, stabilizers, thixotropic agents, spreading agents, and adhesive agents.

Component A is preferably a compound containing oxirane, i.e., an epoxy-functional compound, or a vinyl-ether-functional compound. Suitable oxirane-containing compounds are, in particular, epoxidized terpenes or α-alkenes, cycloaliphatic epoxides, epoxy alcohols, glycidyl ethers and epoxy-functionalized silicones; cycloaliphatic epoxides have proven to be particularly advantageous. It is preferred to use compounds having $\geq 2$ epoxide groups per molecule.

Basically, all vinyl-ether-functionalized hydroxyl compounds can be considered as vinyl-ether-functional compounds. Suitable compounds are, in particular, cyclohexane-dimethylol divinyl ether, triethylene glycol divinyl ether, butane-dioldivinyl ether, bis(4-vinyloxybutyl)-isophthalate, bis(4-vinyloxybutyl)-succinate, bis(4-vinyloxymethylcyclohexyl-methyl)-glutarate and hydroxybutyl monovinyl ether or vinyl-ether-functionalized hydroxypolyurethanes having an aliphatic or aromatic basic structure. It is preferred to use compounds having $\geq 2$ vinyl ether groups per molecule.

The reaction resin mixtures can additionally contain compounds containing hydroxyl groups, i.e., polyfunctional hydroxyl compounds, which, in the context of a chain transfer reaction, participate in the cationic reaction mechanism. Compounds of this type are, in particular, polyalkylene polyols, polyoxyalkylene polyols and cycloaliphatic hydroxyl compounds; polyfunctional hydroxyl compounds having $\geq 2$ hydroxyl groups per molecule are preferred. The use of compounds containing hydroxyl groups has proven advantageous for increasing reactivity and conversion and for elasticizing the resulting molded materials.

The reaction resin mixtures according to the present invention can be hardened both by irradiation using UV light as well as thermally. In areas inaccessible to light or such areas that, in accordance with the method, can only be partially cured using UV light, the hardening can be accomplished through a rise in temperature, either simultaneously with the UV irradiation or in a subsequent process. The hardening temperature lies generally between 80 and 200° C., preferably about 80 to 150° C.

For the UV irradiation, in principle, all conventional UV sources can be used, such as xenon, tungsten, mercury, and metal halogenide radiation emitters; in addition, UV lasers may be used. The laser beam can be focussed with the aid of an optical system; the UV emission can be either constant or pulsed. It is preferred to use UV light having wavelengths of from 300 to 400 nm. It is possible to cure layers made of reaction resin mixtures across their entire surface using UV irradiation, or only in locally limited areas. Local limitation of the hardening, for example, can be achieved by irradiating using a mask. A further possibility is to irradiate these areas using a computer-controlled laser beam.

The reaction resin mixtures (made of cationically polymerizable monomers or oligomers and initiators according to the present invention) are suitable for the coating or bonding of component parts, in particular of electronic components and assemblies, and indeed most of all when, in accordance with the method, there exist areas inaccessible to light and/or the depth of penetration of the UV light is too slight for a complete cure. For example, this is the case when non-transparent parts are bonded; by irradiating the light-accessible edge areas using UV light, a fixing can be achieved, and, by a thermal process, also a hardening between the jointing partners. Reaction resin mixtures which, for modifying the molded-material properties, contain light-diffusing or light-absorbing additives, such as fillers, dyes, pigments and stabilizers, can be superficially or partially hardened by UV irradiation; a complete hardening, in turn, is then possible through a thermal process.

The reaction resin mixtures can also function to produce patterns. For this purpose, a layer made of the reaction resin mixture is produced, through a suitable procedure, and this layer is irradiated using a mask or by a laser beam. The non-irradiated areas are then dissolved out using a suitable solvent.

Preferably, the reaction resin mixtures according to the present invention are used for stereo lithographical production of three-dimensional structures, it being possible to realize plastic models of any complexity on the basis of 3D CAD data. For this purpose, a thin layer of the reaction resin mixture (in a container) is irradiated patternwise using a laser and is hardened, in this context, at those places which correspond to the lower partial surfaces of the model to be produced. In this context, a first layer of the three-dimensional structure is formed. Subsequently, on top of this first layer, a further thin layer of reaction resin mixture is formed and is then correspondingly irradiated, i.e., hardened. In this way, a second layer of the three-dimensional structure is formed, which bonds to the first layer. These process steps are repeated as often as necessary until the three-dimensional structure is completely constructed, layer by layer. To increase productivity, it is advantageous not to cure the individual partial layers completely using a high dose of UV light, but rather, for example, to cure only the external contour and a grid in the interior, or to set the UV dose by the laser scan rate such that, within the layer, a solidification is attained, but not a complete reaction. In these cases, the finished model can also be cured in the interior, following the layer-by-layer build-up and, if necessary, after a cleaning (after removal from the container) by annealing and/or UV irradiation.

The invention is explained in greater detail on the basis of exemplary embodiments (Fp=melting point).

EXAMPLE 1

Synthesizing S-[2-(benzo[b]pyran-2-one-3-yl)-2-oxo]-ethyl-thiolanium-hexafluoroantimonate (Initiator 1)

a) Production of ω-bromine-3-acetyl cumarin

A solution of 8 g $Br_2$ in 50 ml diethyl ether is added dropwise, while stirring, to a solution of 10 g 3-acetyl cumarin (53 mmol) in 250 ml diethyl ether, and is then stirred for another hour. The ω-bromine-3-acetyl cumarin that precipitates out in the course of the reaction is filtered with suction, washed with diethyl ether, and dried in a vacuum.

Fp: 163° C.

Yield: 13 g (92%)

b) Production of S-[2-(Benzo[b]pyran-2-one-3-yl)-2-oxo]-ethyl-thiolanium-bromide 5 g ω-bromine-3-acetyl cumarin (19 mmol) is added to the equimolar quantity of tetrahydrothiophene in 50 ml of acetone, and then is stirred for an hour at room temperature. After approximately 24 hours, the precipitate is filtered with suction, washed with cold acetone, and dried in a vacuum.

c) Anion exchange

To carry out the anion exchange, the sulfonium bromide is dissolved in as little methanol as possible and is added to the equimolar quantity of sodium hexafluoroantimonate ($Na[SbF_6]$), which is dissolved in methanol, while being slightly heated. The precipitate is filtered with suction and is recrystallized repeatedly in methanol or in a methanol/acetone-solvent mixture, until the halogenide test using $AgNO_3$ is negative.

Fp: >240° C. (with decomposition)

Yield: 70%

EXAMPLE 2

Synthesizing S-[2-(8-methoxy-benzo[b]pyran-2-one-3-yl)-2-oxo]-ethyl-thiolanium-hexafluoroantimonate (Initiator 2)

a) Production of 3-acetyl-(8-methoxy)-cumarin 7.6 g 3-methoxysalicylaldehyde (50 mmol) and 7.8 g acetoacetic ester (60 mmol) are dissolved in 50 ml of ethanol, and, after a catalytic quantity of pyridine is added (approx. 10 drops), is then heated to 60° C. for one hour. In the course of the reaction, the 3-acetyl-(8-methoxy)-cumarin which has formed precipitates almost quantitatively.

Fp: 169° C.

Yield: 9.8 g (90%)

b) Production of ω-bromine-3-acetyl-(8-methoxy)-cumarin

The bromination of 3-acetyl-(8-methoxy)-cumarin to ω-bromine-3-acetyl-(8-methoxy)-cumarin is carried out as in Example 1a.

Fp: 165° C.

Yield: 81% c) Production of S-[2-(8-methoxy-benzo[b]pyran-2-one-3-yl)-2-oxo]-ethyl-thiolanium-bromide The reaction yielding the sulfonium bromide by alkylation of tetrahydrothiophene using ω-bromine-3-acetyl-(8-methoxy)-cumarin takes place as in Example 1b.

d) Anion exchange

The anion exchange takes place as in Example 1c.

Fp: 234° C.

Yield: 40%

EXAMPLE 3

Synthesizing S-[2-(7-methoxy-benzo[b]pyran-2-one-3-yl)-2-oxo]-ethyl-thiolanium-hexafluoroantimonate (Initiator 3)

a) Production of 3-acetyl-(7-methoxy)-cumarin

A reaction corresponding to Example 2a takes place using 4-methoxy-salicylaldehyde.

b) Production of ω-bromine-3-acetyl-(7-methoxy)-cumarin

The bromination of 3-acetyl-(7-methoxy)-cumarin to ω-bromine-3-acetyl-(7-methoxy)-cumarin is carried out as in Example 1a.

Fp: 208–210° C.

Yield: 75% c) Production of S-[2-(7-methoxy-benzo[b]pyran-2-one-3-yl)-2-oxo]-ethyl-thiolanium-hexafluoroantimonate 2.7 g of tetrahydrothiophene (30 mmol) is added to 3 g of ω-bromine-3-acetyl-(7-methoxy)-cumarin (10 mmol), and is then heated in a water bath to 50° C. within 30 minutes. Subsequently, 150 ml methanol is added, and then is stirred for another 30 min at 50° C. After being cooled to room temperature, a solution of 2.6 g sodium hexafluoroantimonate (10 mmol) is added in 30 ml methanol; the sulfonium hexafluoroantimonate precipitates out in the process. The precipitate is filtered with suction and is repeatedly recrystallized until the halogenide test using $AgNO_3$ is negative.

Fp: 203° C.

Yield: 3.8 g (70%)

EXAMPLE 4

Synthesizing S-[2-(6-methoxy-benzo[b]pyran-2-one-3-yl)-2-oxo]-ethyl-thiolanium-hexafluoroantimonate (Initiator 4)

a) Production of 3-acetyl-(6-methoxy)-cumarin

A reaction corresponding to Example 2a takes place using 5-methoxy-salicylaldehyde.

Fp: 174° C.

Yield: 95% b) Production of ω-bromine-3-acetyl-(6-methoxy)-cumarin

The brominization of 3-acetyl-(6-methoxy)-cumarin to ω-bromine-3-acetyl-(6-methoxy)-cumarin is carried out as in Example 1a.

Fp: 142° C.

Yield: 64% c) Production of S-[2-(6-methoxy-benzo[b]pyran-2-one-3-yl)-2-oxo]-ethyl-thiolanium-bromide The reaction yielding the sulfonium bromide by alkylation of tetrahydrothiophene using ω-bromine-3-acetyl-(6-methoxy)-cumarin takes place as in Example 1b.

d) Anion exchange

The anion exchange takes place as in Example 1c.

Fp: 243–245° C.

Yield: 42%

Table 1 gives an overview of the substituents and of the purity of the compounds according to Examples 1 through 4, which have the following structure:

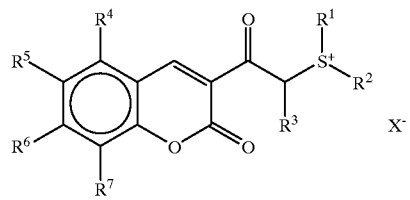

TABLE 1

|  | Initiator 1 | Initiator 2 | Initiator 3 | Initiator 4 |
|---|---|---|---|---|
| $R^1$ | $R^1$ and $R^2$ together form a tetramethylene group | | | |
| $R^2$ | —(CH$_2$)$_4$— | | | |
| $R^3$ | —H | —H | —H | —H |
| $R^4$ | —H | —H | —H | —OCH$_3$ |
| $R^5$ | —H | —H | —OCH$_3$ | —H |
| $R^6$ | —H | —OCH$_3$ | —H | —H |
| $R^7$ | —H | —H | —H | —H |
| $X^-$ | $SbF_6^-$ | $SbF_6^-$ | $SbF_6^-$ | $SbF_6^-$ |
| Elementary analysis | | | | |
| C[%] "cal." | 35.2 | 35.5 | 35.5 | 35.5 |
| C[%] "fnd." | 34.9 | 34.7 | 35.2 | 34.0 |
| H[%] "cal." | 2.94 | 3.14 | 3.14 | 3.14 |
| H[%] "fnd." | 2.96 | 3.2 | 3.5 | 3.3 |
| S[%] "cal." | 6.3 | 5.9 | 5.9 | 5.9 |
| S[%] "fnd." | 6.3 | 6.1 | 6.1 | 6.0 |

"cal." = calculated,
"fnd." = found

Table 2, in which the UV absorption in dimethylformamide is represented, shows, on the basis of the extinction coefficients, that the compounds according to Examples 1 to 4 are capable of effectively absorbing UV light at 366 nm (mercury line). A conventional triarylsulfonium salt (UVI 6974, Union Carbide), on the other hand, only absorbs in negligible amounts at this wavelength (example for purposes of comparison).

TABLE 2

|  | Extinction coefficient at 366 nm [1/g · cm] | Absorption maximum Wavelength [nm] | Extinction coefficient [1/g · cm] |
|---|---|---|---|
| Triarylsulfonium salt (comp. ex.) | 0.8 | 308 | 9.9 |
| Initiator 1 | 13.8 | 313/349 | 23.5/16.9 |
| Initiator 2 | 9.4 | 331 | 27.2 |
| Initiator 3 | 36.5 | 375 | 39 |
| Initiator 4 | 8.2 | 311/391 | 23.1/10.6 |

The following examples 5 to 11 show that the initiators according to the present invention can be used advantageously for hardening cationically polymerizable reaction resin mixtures. The composition of resin mixtures (in parts by weight) is indicated in Table 3.

EXAMPLES 5 TO 8

For producing a resinous base, equal parts by weight of bisphenol-A-diglycidyl ether and cyclohexane-dimethylol divinyl ether are dissolved, while being stirred and heated to approximately 50° C. From each initiator and 1,2-propylene carbonate, a solution is produced, to which is added the quantity of a resinous base corresponding to the composition in Table 3. The reaction resin mixture yielded is then stirred at room temperature, with light excluded, and is homogenized.

The results given in Table 4 regarding the thermal reactivity of the reaction resin mixtures show that the mixtures of initiators according to the present invention and cationically polymerizable components are stable in storage and can be cured by purely thermal means.

EXAMPLES 9 TO 11

For producing a resinous base, 95 parts by weight of bis-(epoxycyclohexyl-methyl)-adipate and 5 parts by weight of trimethylol propane are dissolved while being heated to approximately 50° C. and stirred. From each initiator and 1,2-propylene carbonate, a solution is produced, to which is added the quantity of a resinous base corresponding to the composition in Table 3. The resulting reaction resin mixture is then stirred at room temperature, with light excluded, and is homogenized.

The results presented in Table 5 in regard to the reactivity of the reaction resin mixtures in response to UV irradiation show that the mixtures of the initiators according to the present invention and cationically polymerizable components can be hardened using UV irradiation.

TABLE 3

| Example | 5 | 6 | 7 | 8 | 9 | 10 | 11 |
|---|---|---|---|---|---|---|---|
| Bisphenol-A-diglycidyl ether | 50 | 50 | 50 | 50 | — | — | — |
| Cyclohexane-dimethylol-divinyl ether | 50 | 50 | 50 | 50 | — | — | — |
| Bis(epoxycyclohexyl-methyl)-adipate | — | — | — | — | 95 | 95 | 95 |
| Trimethylol-propane | — | — | — | — | 5 | 5 | 5 |
| 1,2-propylene carbonate | 1.6 | 1.6 | 1.6 | 1.6 | 1.6 | 1.6 | 1.6 |
| Initiator 1 | 0.4 | — | — | — | — | — | — |
| Initiator 2 | — | 0.4 | — | — | 0.4 | — | — |
| Initiator 3 | — | — | 0.4 | — | — | 0.4 | — |
| Initiator 4 | — | — | — | 0.4 | — | — | 0.4 |

TABLE 4

| Example | 5 | 6 | 7 | 8 |
|---|---|---|---|---|
| Stability in storage (time until viscosity doubling) | >6 months | >6 months | >6 months | >6 months |
| Results from DSC tests (rate of heating 10 K/min) | | | | |
| Onset [° C.] | 111 | 112 | 108 | 110 |
| Peak maximum [° C.] | 118 and 188 | 124 and 188 | 118 and 186 | 120 and 183 |
| Enthalpy [J/g] | 430 | 420 | 410 | 470 |

TABLE 5

| Example | 9 | 10 | 11 |
|---|---|---|---|
| Results of photo-DSC tests (isothermal measuring course at 40° C.; irradiation during the measuring using UV light with wavelength 351 nm, i.e., line of argon-ion laser) | | | |
| Onset [s] | 1.62 | 1.38 | 2.1 |
| Time until peak maximum [s] | 7.92 | 9.0 | 11.6 |
| Peak level [W/g] | 3.63 | 3.48 | 1.99 |
| Enthalpy [J/g] | 161 | 162 | 149 |

What is claimed is:

1. A reaction resin mixture, comprising:

component A selected from cationically polymerizable monomer or oligomer, or a mixture of cationically polymerizable monomer and cationically polmerizable oligomer; and 0.01 to 10% by mass, with respect to component A, of an initiator comprising a compound having the structure:

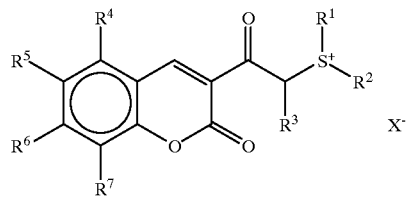

where:

$R^1$ and $R^2$ are alkyl having 1 to 9 C atoms, or cycloalkyl having 4 to 9 C atoms, or they together form a divalent aliphatic group having 4 to 7 C atoms, $R^3$ is H, or alkyl having 1 to 9 C atoms, $R^4$, $R^5$, $R^6$, and $R^7$ are H, alkyl having 1 to 9 C atoms, or alkoxy having 1 to 9 C atoms, $X^-$ is a non-nucleophilic anion, comprising hexafluoroantimonate, -arsenate or -phosphate, or tetraphenylborate, tetra(perfluorophenyl) -borate or trifluoromethane sulfonate (component B).

2. The reaction resin mixture according to claim 1, further comprising a filler, pigment or additive.

3. The reaction resin mixture according to claim 1, wherein component A is an oxirane-containing compound.

4. The reaction resin mixture according to claim 3 wherein the oxirane-containing compound is a compound having at least two epoxide groups per molecule.

5. The reaction resin mixture according to claim 3, wherein the oxirane-containing compound is selected from the group consisting of an epoxidized terpene, α-alkene, a cycloaliphatic epoxide, an epoxy alcohol, a glycidyl ether and an epoxy-functionalized silicone.

6. The reaction resin mixture according to claim 1, wherein component A is a vinyl-ether-functional compound.

7. The reaction resin mixture according to claim 6, wherein the vinyl-ether-functional compound has at least two vinyl ether groups per molecule.

8. The reaction resin mixture according to claim 1, further comprising a polyfunctional hydroxyl compound.

9. A reaction resin mixture, comprising:

a cationically polymerizable monomer or oligomer, or a cationically polymerizable monomer and a cationically polymerizable oligomer (component A), wherein the component A is an oxirane-containing compound; and 0.01 to 10% by mass, with respect to component A, of an initiator comprising a compound having the structure:

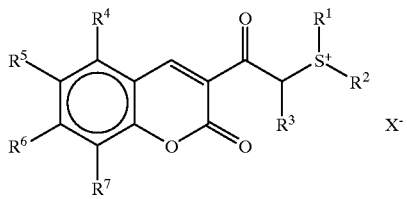

where:

R¹ and R² are alkyl having 1 to 9 C atoms, or cycloalkyl having 4 to 9 C atoms, or they together form a divalent aliphatic group having 4 to 7 C atoms, R³ is H, or alkyl having 1 to 9 C atoms, R⁴, R⁵, R⁶, and R⁷ are H, alkyl having 1 to 9 C atoms, or alkoxy having 1 to 9 C atoms, X⁻ is a non-nucleophilic anion, comprising hexafluoroantimonate, -arsenate or -phosphate, or tetraphenylborate, tetra(perfluorophenyl)-borate or trifluoromethane sulfonate (component B).

10. A reaction resin mixture, comprising:

a cationically polymerizable monomer or oligomer, or a cationically polymerizable monomer and a cationically polymerizable oligomer (component A), wherein the component A is a vinyl-ether-functional compound; and 0.01 to 10% by mass, with respect to component A, of an initiator comprising a compound having the structure:

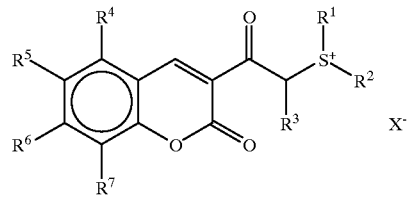

where:

R¹ and R² are alkyl having 1 to 9 C atoms, or cycloalkyl having 4 to 9 C atoms, or they together form a divalent aliphatic group having 4 to 7 C atoms, R³ is H, or alkyl having 1 to 9 C atoms, R⁴, R⁵, R⁶, and R⁷ are H, alkyl having 1 to 9 C atoms, or alkoxy having 1 to 9 C atoms, X⁻ is a non-nucleophilic anion, comprising hexafluoroantimonate, -arsenate or -phosphate, or tetraphenylborate, tetra(perfluorophenyl)-borate or trifluoromethane sulfonate (component B).

* * * * *